United States Patent [19]

Sakai

[11] Patent Number: 5,331,309
[45] Date of Patent: Jul. 19, 1994

[54] DRIP DETECTING DEVICE AND DRIP ALARMING DEVICE AND DRIP RATE CONTROL DEVICE WHICH INCORPORATE DRIP DETECTING DEVICE

[75] Inventor: Hiroshi Sakai, Kanagawa, Japan

[73] Assignee: Terumo Kabushiki Kaisha, Tokyo, Japan

[21] Appl. No.: 957,452

[22] Filed: Oct. 7, 1992

Related U.S. Application Data

[63] Continuation of Ser. No. 648,839, Jan. 31, 1991, abandoned.

[30] Foreign Application Priority Data

Feb. 6, 1990 [JP] Japan .................. 2-25128

[51] Int. Cl.$^5$ .............................. G08B 21/00
[52] U.S. Cl. ...................... 340/606; 604/31; 73/861.41; 128/DIG. 13
[58] Field of Search .............. 340/606, 619; 73/293, 73/861.41; 128/DIG. 13; 604/65, 31

[56] References Cited

U.S. PATENT DOCUMENTS

| | | | |
|---|---|---|---|
| 4,173,224 | 11/1979 | Marx et al. | 604/65 |
| 4,286,590 | 9/1981 | Murase | 128/DIG. 13 X |
| 4,328,801 | 5/1982 | Marx et al. | 604/65 |
| 4,432,761 | 2/1984 | Dawe | 73/861.41 X |
| 4,432,762 | 2/1984 | Dawe | 73/861.41 X |
| 4,509,943 | 4/1985 | Hanazawa | 128/DIG. 13 X |
| 4,680,977 | 7/1987 | Conero et al. | 73/861.41 |
| 4,720,636 | 1/1988 | Benner, Jr. | 128/DIG. 13 X |
| 4,936,828 | 6/1990 | Chiang | 604/65 |

FOREIGN PATENT DOCUMENTS

| | | |
|---|---|---|
| 84278/82 | 6/1983 | Australia . |
| 199919 | 5/1986 | European Pat. Off. . |
| 3806800 | 9/1988 | Fed. Rep. of Germany . |

Primary Examiner—Jeffery A. Hofsass
Attorney, Agent, or Firm—Beveridge, DeGrandi, Weilacher & Young

[57] ABSTRACT

A drip detecting device for detecting drips dropping in a drip cylinder, includes an image detecting portion disposed in the vicinity of the outer wall surface of the drip cylinder for detecting the state in the drip cylinder as an image, and a drip detecting portion for detecting a drip dripping in the drip cylinder on the basis of the image. Disclosed also is a drip alarming device which includes a drip rate detecting portion for detecting the rate of dripping on the basis of the data detected by the drip detecting device, a determining portion for determining whether the detected dripping rate is proper, and a generating portion for generating an alarm in accordance with the result of the determination. A drip rate control device also is detected which has a drip rate detecting portion for detecting the rate of dripping on the basis of the data detected by the drip detecting device, and a drip rate control portion for controlling the drip rate to a required rate. The drip detecting device can detect drips without fail and without being affected by any change in the state of the drip cylinder and has a light-receiving portion which does not receive external disturbance light. These advantages are obtained also in the drip alarming device and the drip rate control device incorporating the drip detecting device.

5 Claims, 5 Drawing Sheets

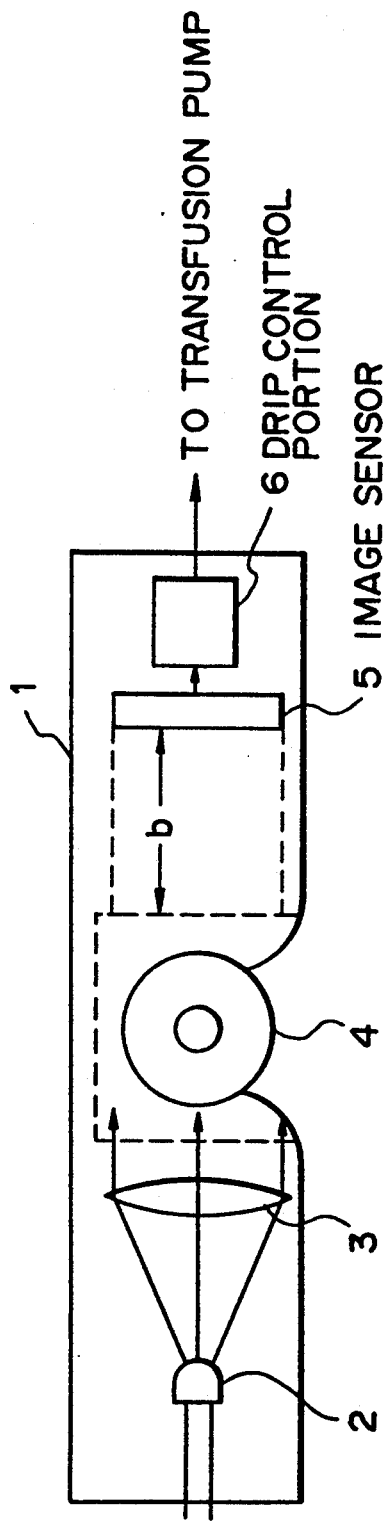
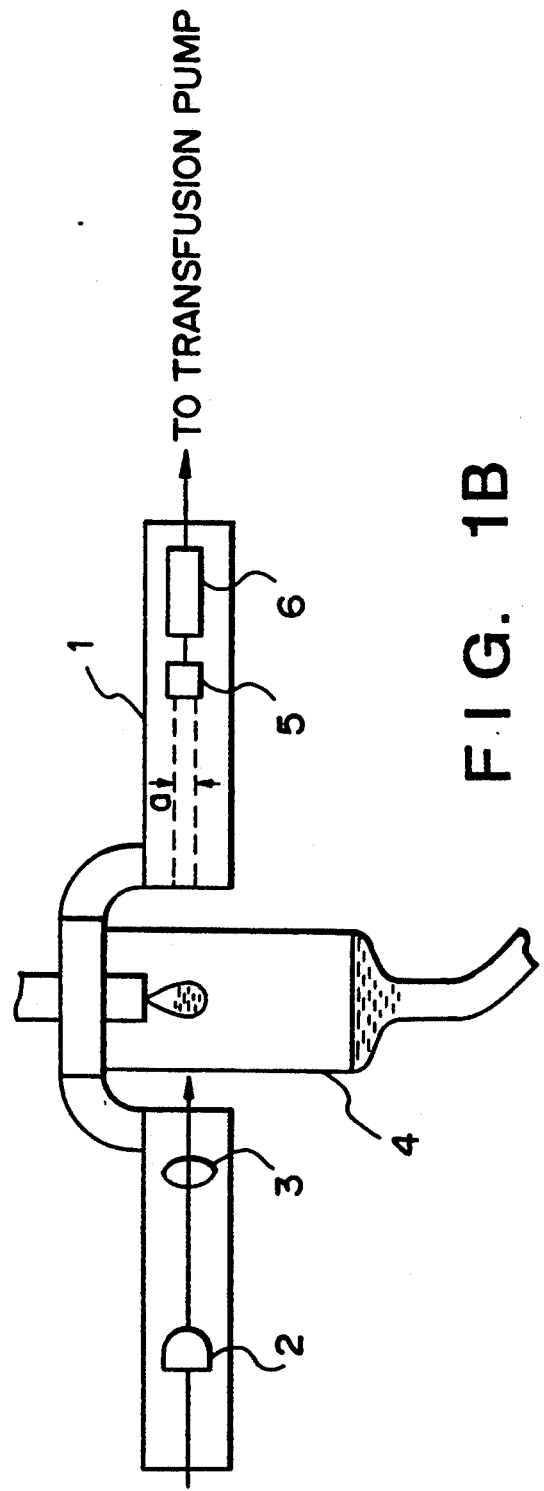
FIG. 1A
FIG. 1B

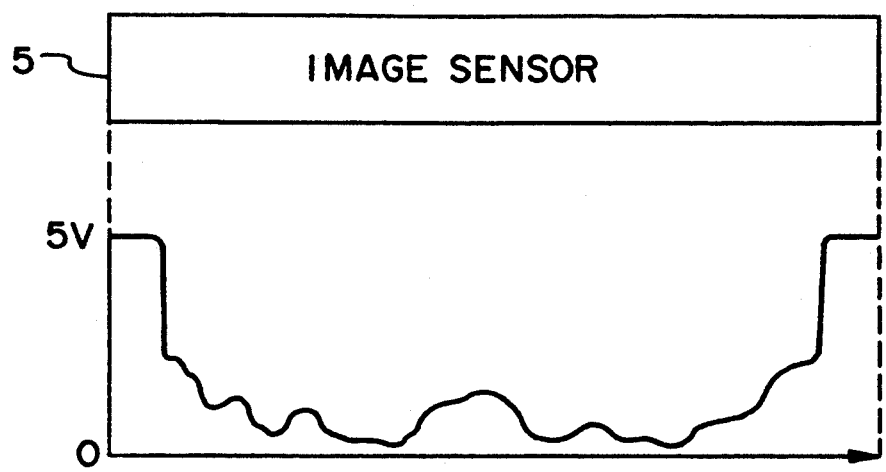
F I G. 4A
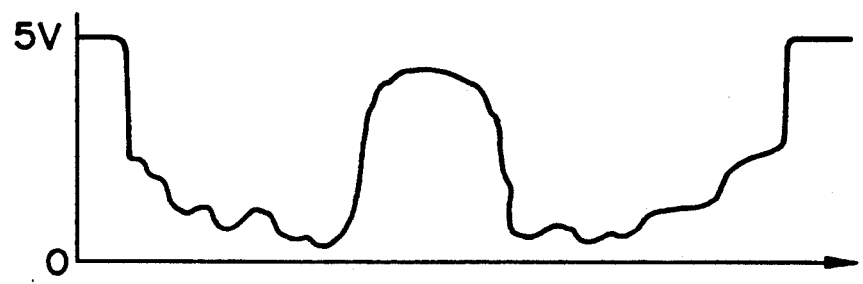
F I G. 4B
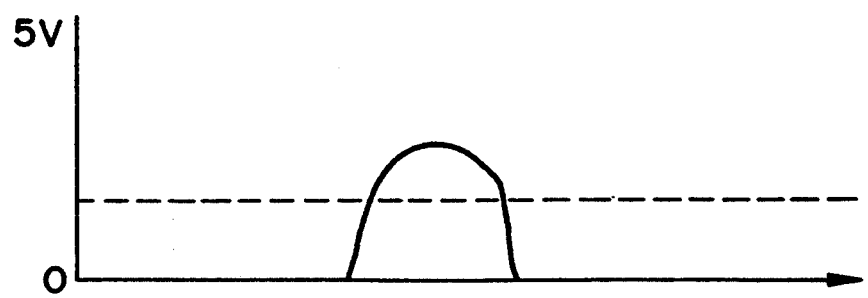
F I G. 4C

DRIP DETECTING DEVICE AND DRIP ALARMING DEVICE AND DRIP RATE CONTROL DEVICE WHICH INCORPORATE DRIP DETECTING DEVICE

This application is a continuation of application Ser. No. 07/648,839, filed Jan. 31, 1991, now abandoned.

BACKGROUND OF THE INVENTION

1. Field of the Invention

The present invention relates to a drip detecting device and also to a drip alarming device and a drip rate control device which incorporate the drip detecting device.

2. Description of the Related Arts

As shown in FIG. 5, a known drip detecting device has a combination of a light-emitting diode 51 and a photodiode (or phototransistor) 54. A light emitted from the light-emitting diode 51 is collimated into a beam through the lens 52 which is introduced to a lens 53 through a drip cylinder, the lens 53 converging the light onto the photodiode or phototransistor 54. The drips are detected by the photodiode or phototransistor 54 through a change in the quantity of light which is caused by passage of the drip through the drip cylinder. Namely, as shown in FIG. 6A, the passage of the droplet, i.e., drip, is confirmed when the output level of the photodiode 54 has exceeded a predetermined threshold. However, since only one semiconductor element is used at the light-receiving side so as to receive converged light, the accuracy of detection tends to be degraded during long use. Namely, the quantity of light received by the light-receiving element is progressively reduced by deposition of fine liquid droplets to the inner surface of the drip cylinder due to splashing of liquid or by clouding of the wall of the drip cylinder due to change in temperature. In consequence, the difference between the output voltage level during a drip passing through the drip cylinder and the output voltage level with no drip becomes small to reduce the S/N ratio as shown in FIG. 6B, making it difficult to accurately detect the drips. In addition, detection error is often caused due to incidence of strong external disturbance light such as solar light into the light-receiving element.

SUMMARY OF THE INVENTION

Accordingly, an object of the present invention is to provide a drip detecting device which can detect drips without fail regardless of any change in the state of the drip cylinder, thereby overcoming the above-described problems of the prior art.

Another object of the present invention is to provide a drip detecting device having a light-receiving portion which does not receive any external disturbance light.

Other objects of the invention are to provide a drip alarming device and a drip rate control device which makes use of the drip detecting device.

According to the present invention, there is provided a drip detecting device for detecting drips dropping in a drip cylinder, comprising image detecting means disposed in the vicinity of the outer wall surface of said drip cylinder for detecting the state in said drip cylinder as an image, and drip detecting means for detecting a drip dropping in said drip cylinder on the basis of the image detected by said image detecting means.

In a preferred form of the invention, the image detecting means comprises a light source means including a light source having a peak of light emission in the visible ray range and a collimator lens combined with the light source for generating collimated light, and an image sensor for receiving the collimated light which passes through said drip cylinder.

In another preferred form, the drip detecting device further comprises a slit disposed on the incident side of said image sensor, said slit having a length not smaller than a predetermined value and a height not greater than a predetermined height so as to restrict incidence of external disturbance light.

The invention also provides a drip alarming device comprising drip rate detecting means for detecting the rate of dripping on the basis of the data detected by said drip detecting device determining means for determining whether the detected dripping rate is predetermined value; and generating means for generating an alarm in accordance with the result of the determination by said determining means.

According to the invention, provided also is a drip rate control device comprising drip rate detecting means for detecting the rate of dripping on the basis of the data detected by said drip detecting device and drip rate control means for controlling the drip rate to a required rate in accordance with the drip rate detected by said drip rate detecting means.

According to these arrangements, the noise components such as clouding of the drip cylinder wall are picked up as images and removed so that presence of a drip can be detected accurately. In addition, by optimizing the position of the image sensor, it is possible to significantly restrict incidence of external disturbance light, thus improving anti-noise characteristics.

The image sensor and the drip rate control means may be integrated so that control of drip rate is made possible only by setting the drip detecting device.

Other objects, features and advantages of the present invention will become clear from the following description of the preferred embodiments when the same is read in conjunction with the accompanying drawings.

BRIEF DESCRIPTION OF THE DRAWINGS

FIG. 1A is a top plan view of a drip control device in accordance with the present invention;

FIG. 1B is a front elevational view of a drip control device shown in FIG. 1A;

FIGS. 4A to 4C are illustrations of examples of operation for detecting drips, performed by an embodiment of the present invention;

DESCRIPTION OF THE PREFERRED EMBODIMENTS

Figure 2:
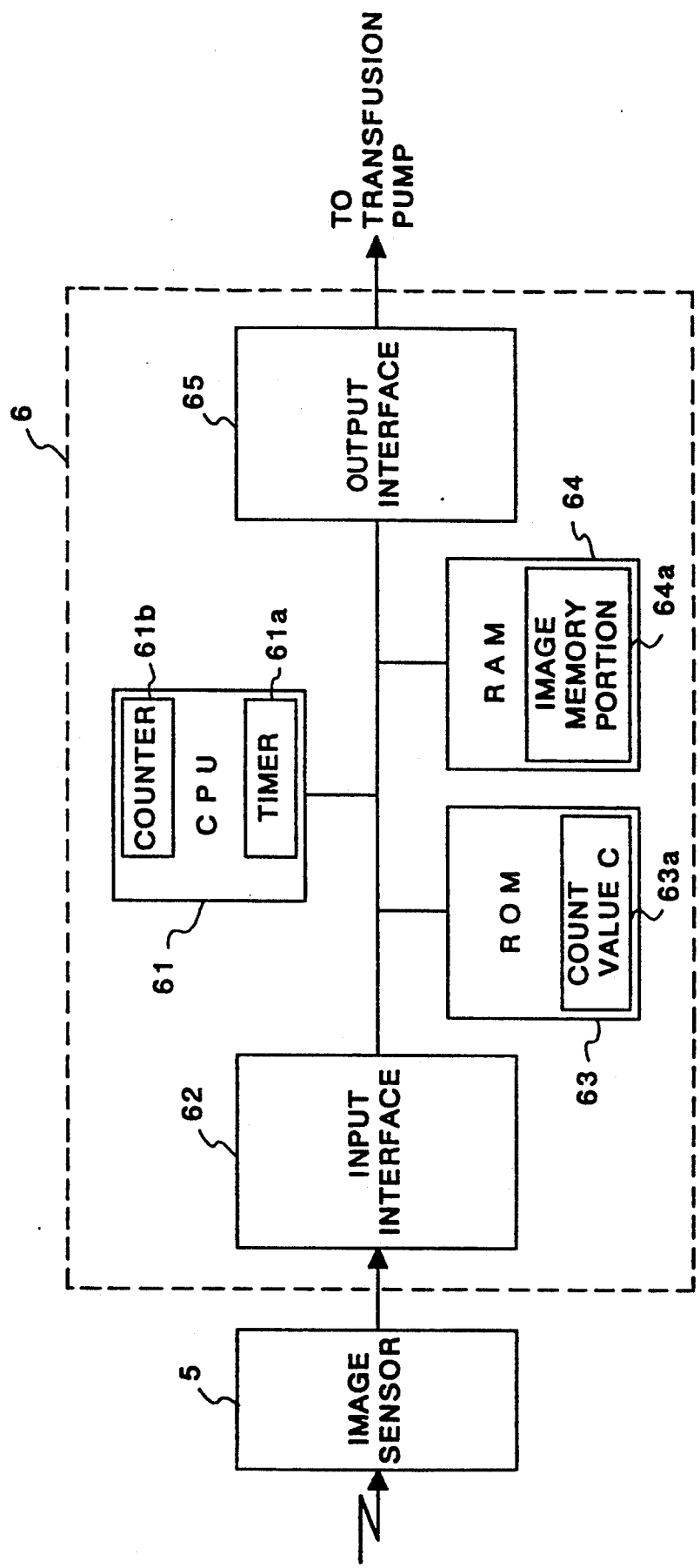
FIG. 2 is a block diagram showing the construction of a drip control portion of the drip control device.

Embodiments of the present invention will be described in detail with reference to the accompanying drawings.

FIG. 1A is a top plan view and FIG. 1B is a front elevational view of an embodiment of the drip detecting device of the present invention which is adapted to be used in combination with a transfusion pump (not shown) connected thereto.

The device has a case 1 encasing an LED 2, a collimator lens 3 for forming a collimated light beam, an image sensor 5 and a drip control portion 6 including a microprocessor. The case 1 can slide so as to pinch a drip cylinder 4 at both sides as illustrated. The LED 2 is adapted to be lit in accordance with instructions given by the microprocessor of the drip control portion 6. Meanwhile, data from the image sensor 5 is delivered to the microprocessor of the drip control portion 6, so that the microprocessor determines whether a drip is passing through the drip cylinder on the basis of pattern matching. The microprocessor then compares the detected time interval of dripping and the dripping time interval corresponding to a desired flow rate, and conducts the control of operation of the transfusion pump in accordance with the result of the comparison.

FIG. 2 is a block diagram of the construction of the drip control portion 6.

The data from the image sensor 5, in the form of digital data, is stored in an image storage area 64a of a RAM 64 through an input interface 62. A CPU 61 detects the rate of drip by using signals from a timer 61a, counter 61b and a count value 63a, in accordance with a control program stored in a ROM 63, and delivers a signal for controlling the drip rate to the transfusion pump (not shown) through an interface 65.

Figure 3:
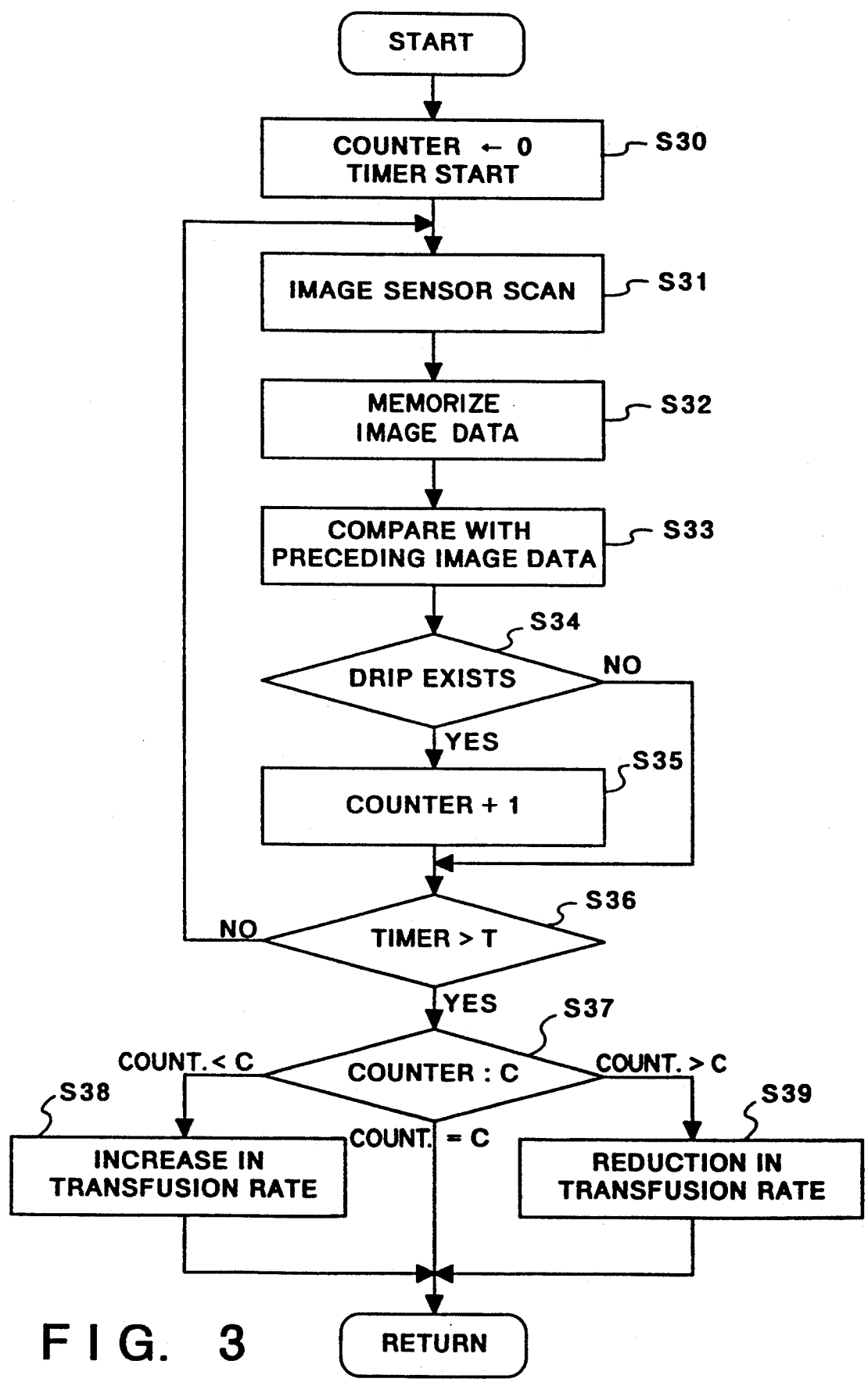
FIG. 3 is a flow chart showing the control process performed by the drip control portion.
Figure 5:
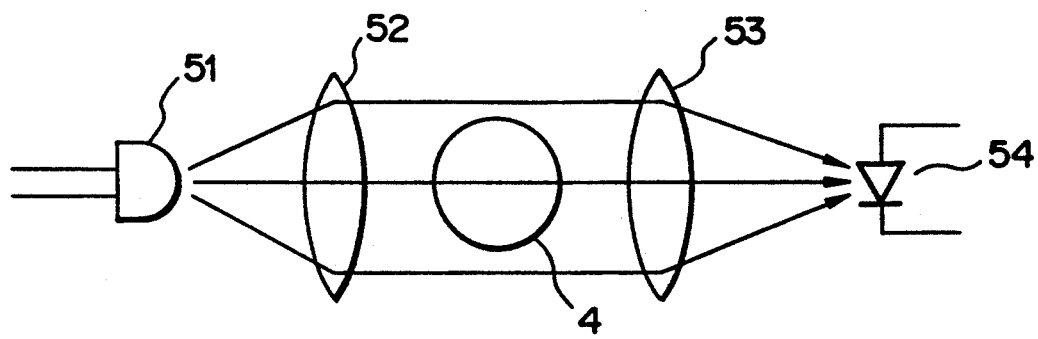
FIG. 5 is a schematic illustration of a conventional drip detecting device.
Figure 6A:
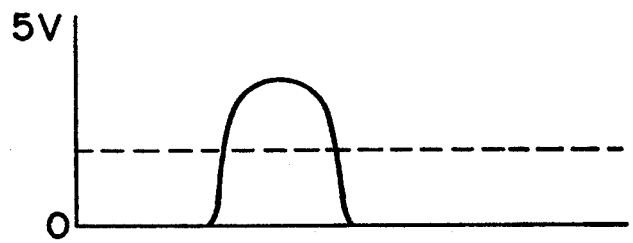
FIGS. 6A and 6B are illustrations of operation performed by the conventional drip detecting device.
Figure 6B:
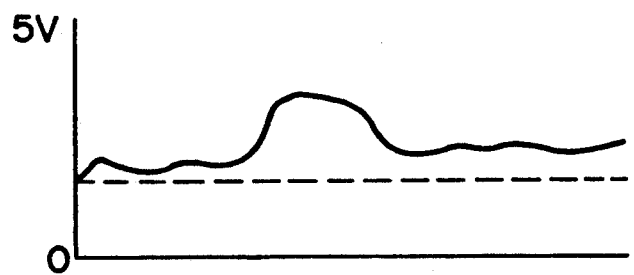

FIG. 3 is a flow chart of a control process performed by the drip control portion 6. For the purpose of clarification, this figure shows only a drip-control sub-routine.

In Step S30, the counter 61b is set to zero and then the timer 61a is started. Subsequently, in Step S31, the image sensor is scanned and the image data obtained through the scanning is stored in the image storage area 64a in Step S32. In Step S33, the presently-obtained image data is compared with the image data stored through the preceding scanning. In Step S34, a check is conducted as to whether there is any drip dropping through the drip cylinder.

The method of detecting drip will be described with reference to FIGS. 4A to 4C. FIG. 4A shows input data as obtained from the image sensor 5 when there is no drip. Signals corresponding to tiny droplets attaching to the wall of the drip cylinder due to splashing of liquid and clouding of the cylinder wall are included in the data shown in FIG. 4A. FIG. 4B shows input data as obtained when a drip exists. It will be seen that the signal generated by the presence of the drip is added to the output shown in FIG. 4A. By determining the difference between the output shown in FIG. 4A and that shown in FIG. 4B, it is possible to obtain the output component which purely corresponds to the drip, i.e., the output which is devoid of the components corresponding to the tiny droplets attaching to the drip cylinder wall and clouding of the cylinder wall. According to this method, it is possible to detect the drip even when the cylinder wall is colored, although in the described embodiment the wall is transparent.

Referring again to FIG. 3, when it is determined that a drip exists, the process proceeds to Step S35 in which the counter 61b is incremented by one. In Step S36, a judgment is conducted as to whether the time counted by the timer 61a has exceeded a predetermined time T. If the time T is not exceeded, the process returns to Step S31 to repeat Steps S31 to S36.

Conversely, if the time T has been exceeded, the process proceeds to Step S37 which compares the content of the counter 61b with the count value C. If both values are equal, no control is conducted since in this case the dripping rate is proper. However, when the content of the counter 61b is smaller than the count value C, the process proceeds to Step S38 in which a signal is delivered to the transfusion pump so as to increase the transfusion rate. Conversely, if the count value C is exceeded by the content of the counter 61b, a signal is delivered to the transfusion pump so as to reduce the transfusion rate in Step S39. The process then proceeds to a returning step. The count value C may be externally adjustable so as to enable free setting of the transfusion rate.

Showing in FIGS. 1A and 1B, a slit of length "b" not smaller than a predetermined value and a height "a" not greater than a predetermined value is provided on the light-incident side of the image sensor 5 so that the image sensor 5 receives only collimated light directed through the drip cylinder. The slit thereby excludes external disturbance light so as to enable a stable detection of drips. The slit and the image sensor 5 have widths which are similar to (slightly exceeding in FIG. 1A) the diameter of the drip cylinder 4.

As will be understood from the foregoing description, according to the present invention, a drip detecting device is provided which is not affected by attaching of tiny droplets to the drip cylinder wall and clouding of the cylinder and which is not sensitive to external disturbance light, by virtue of the use of an image sensor for the detection and specific arrangement of the image sensor. By using this drip detecting device, it is possible to obtain a drip alarming device which can accurately determine whether the dripping rate is proper or abnormal. In addition, since the microprocessor is incorporated in the drip detecting device, it is possible to obtain a drip rate control device which can control the dripping rate always to the proper range only by the setting of the drip detecting device.

Thus, the present invention provides a drip detecting device which can accurately detect the state of dripping regardless of any change in the state of the drip cylinder and which has a light-receiving portion which is free from the external disturbance light.

In addition, the present invention provides a drip alarming device which can accurately determine whether the dripping rate is proper or not and which produces an alarm in the event of detection of an abnormal dripping rate.

Furthermore, a dripping rate control device capable of accurately controlling the dripping rate is obtained according to the invention.

It is understood that various changes and modifications may be made in the invention without departing from the spirit and scope of the appended claims which delineate the inventive concepts of the present invention.

What is claimed is:

1. A drip detecting device for detecting drips dropping in a drip cylinder, said device comprising:
   a transparent drip cylinder;
   light source means for directing a beam of collimated light having a width similar to a diameter of the transparent drip cylinder into the transparent drip cylinder;
   image detecting means, comprising an image sensor positioned at an opposite side of the transparent drip cylinder as said light source means, for detecting transmitted light through the drip cylinder as a result of the collimated light directed therein, and for providing image data corresponding to a side view of the drip cylinder from the transmitted light; and drip detecting means for detecting a drip dropping in the transparent drip cylinder by extracting image data representative of the drip from image data representative of a plurality of images provided by said image detecting means, said plurality of images including at least one image when there is no drip in the transparent drip cylinder, and at least one image when there is a drip therein, and said image data representative of the drip being provided by the difference between image data representative of said at least one image when there is no drip and image data representative of said at least one image when there is a drip.

2. A drip detecting device according to claim 1, wherein said light source means includes a light source having a peak of light emission in the visible ray range and a collimator lens combined with said light source for generating said collimated light, and an image sensor having a width similar to a diameter of the transparent drip cylinder for receiving collimated light from said collimator lens which passes through said transparent drip cylinder as the transmitted light.

3. A drip detecting device according to claim 1, wherein said image detecting means further comprises a slit disposed on an incident side of said image sensor for passing the transmitted light therethrough, said slit having a length in a direction of the transmitted light not smaller than a predetermined value and a height not greater than a predetermined value so as to restrict incidence of external disturbance light.

4. A drip alarm device for generating an alarm signal when a dripping rate in a drip cylinder is not a proper rate, said device comprising:

a drip detecting device for detecting drips dropping in a drip cylinder, said drip detecting device including a transparent drip cylinder, light source means for directing a beam of collimated light having a width similar to a diameter of the transparent drip cylinder into the transparent drip cylinder, image detecting means, comprising an image sensor positioned at an opposite side of the transparent drip cylinder as said light source means, for detecting transmitted light through the drip cylinder as a result of the collimated light directed therein, and for providing image data corresponding to a side view of the drip cylinder from the transmitted light, and drip detecting means for detecting a drip dropping in the transparent drip cylinder by extracting image data representative of the drip from image data representative of a plurality of images provided by said image detecting means, said plurality of images including at least one image when there is no drip in the transparent drip cylinder, and at least one image when there is a drip therein, and said image data representative of the drip being provided by the difference between image data representative of said at least one image when there is no drip and image data representative of said at least one image when there is a drip;

drip rate detecting means for detecting a drip rate on the basis of drips detected by said drip detecting device;

determining means for determining whether the drip rate is substantially equal to a predetermined value; and generating means for generating an alarm in accordance with a determination result by said determining means.

5. A drip rate control device for controlling a drip rate for drips in a drop cylinder, said device comprising:

a drip detecting device for detecting drips dropping in a drip cylinder, said drip detecting device including a transparent drip cylinder, light source means for directing a beam of collimated light having a width similar to a diameter of the transparent drip cylinder into the transparent drip cylinder, image detecting means, comprising an image sensor positioned at an opposite side of the transparent drip cylinder as said light source means, for detecting transmitted light through the drip cylinder as a result of the collimated light directed therein and for providing image data corresponding to a side view of the drip cylinder from the transmitted light, and drip detecting means for detecting a drip dropping in the transparent drip cylinder by extracting image data representative of the drip from image data representative of a plurality of images provided by said image detecting means, said plurality of images including at least one image when there is no drip in the transparent drip cylinder, and at least one image when there is a drip therein, and said image data representative of the drip being provided by the difference between image data representative of said at least one image when there is no drip and image data representative of said at least one image when there is a drip;

drip rate detecting means for detecting a drip rate on the basis of drips detected by said drip detecting device; and drip rate control means for controlling a drip rate to a required rate in accordance with the drip rate detected by said drip rate detecting means.

* * * * *